US005565479A

United States Patent [19]

Iwaoka et al.

[11] Patent Number: 5,565,479
[45] Date of Patent: Oct. 15, 1996

[54] CONDENSED THIAZOLE DERIVATIVE, PRODUCTION PROCESS THEREOF AND PHARMACEUTICAL COMPOSITION THEREOF

[75] Inventors: Kiyoshi Iwaoka; Hiroyuki Koshio; Hiroyuki Ito; Keiji Miyata; Mitsuaki Ohta, all of Ibaraki, Japan

[73] Assignee: Yamanouchi Pharmaceutical Co., Ltd., Tokyo, Japan

[21] Appl. No.: 403,724

[22] PCT Filed: Sep. 10, 1993

[86] PCT No.: PCT/JP93/01298

§ 371 Date: Apr. 28, 1995

§ 102(e) Date: Apr. 28, 1995

[87] PCT Pub. No.: WO94/06791

PCT Pub. Date: Mar. 31, 1994

[30] Foreign Application Priority Data

Sep. 14, 1992 [JP] Japan ..................... 4-272389

[51] Int. Cl.$^6$ .................. A61K 31/425; C07D 417/04; C07D 417/06
[52] U.S. Cl. .................. 514/366; 548/149; 548/150; 548/151
[58] Field of Search .................. 548/149, 150, 548/151; 514/366

[56] References Cited

U.S. PATENT DOCUMENTS 4,963,689  10/1990  Nagel et al. .................. 548/181
5,130,313   7/1992  Comte et al. .................. 514/253
5,378,706   1/1995  Biziere et al. .................. 514/232.8
5,424,431   6/1995  Ohta et al. .................. 546/114

FOREIGN PATENT DOCUMENTS 0433149  6/1991  European Pat. Off. .
0513387  6/1992  European Pat. Off. .

Primary Examiner—Johann Richter
Assistant Examiner—Laura R. Cross
Attorney, Agent, or Firm—Burgess, Ryan and Wayne

[57] ABSTRACT

Condensed thiazole derivatives useful as 5-HT$_3$ receptor agonists are provided and can be represented by the following formula (I) or a pharmaceutically acceptable salt thereof, a process for the production thereof and a pharmaceutical composition thereof:

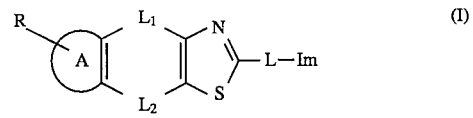

wherein R, A, L$_1$, L$_2$, L, and R$^1$–R$^6$ are defined herein and Im represents a group of the formula:

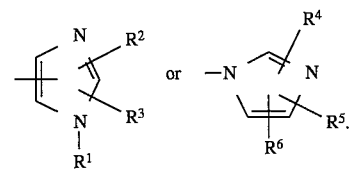

7 Claims, No Drawings

CONDENSED THIAZOLE DERIVATIVE, PRODUCTION PROCESS THEREOF AND PHARMACEUTICAL COMPOSITION THEREOF

This application is a 371 of PCT/J93/01298 filed Sep. 10, 1993, and published as WO94/06791 Mar. 31, 1994.

TECHNICAL FIELD

This invention relates to novel condensed thiazole derivatives useful as pharmaceutical agents especially as a 5-HT$_3$ receptor agonists, to pharmaceutically acceptable salts thereof, to a production process thereof and to a pharmaceutical composition comprising the same as an active ingredient.

BACKGROUND ART

The compounds of the present invention act as an effective and selective agonist for the neuronal serotonin (5-HT) receptor located in the primary afferent nerve of enteric nervous system or central nervous system. This type of receptor is now considered as a 5-HT$_3$ receptor. The compounds of the present invention exert their function by releasing acetylcholine from the efferent nerve ending in the digestive tracts. It is known that stimulation of the acetylcholine receptor in the digestive tracts accelerates motility of the gastrointestinal tracts and improves functional reduction of the gastrointestinal tracts [Goonman and Gilman's, *The Pharmacological Basis of Therapeutics* 8th edition, p.125, (1990), Pergamon Press]. It is also known that the 5-HT$_3$ receptor is present in the presynaptic area of central nervous system and inhibits nervous activities by its stimulation [*J. Neurosci.*, 11, 1881 (1991)].

In consequence, it is considered that a 5-HT$_3$ receptor agonist is useful especially against gastrointestinal disorders.

Though no compound having a selective agonistic activity on the 5-HT$_3$ receptor had been found, the inventors of the present invention reported that thiazole derivatives disclosed in WO 92/07849 possess a selective 5-HT$_3$ receptor agonistic activity.

DISCLOSURE OF THE INVENTION

The inventors of the present invention have continued a further investigation concerning agonistic activities on the 5-HT$_3$ receptors, and found that a 2-(imidazolyl)alkylene-condensed thiazole derivative shows an excellent 5-HT$_3$ receptor agonistic activity as a result of studies on the synthesis of compounds having a 5-HT$_3$ receptor agonistic activity with taking notice of the contractile effects of 5-HT mediated through the 5-HT$_3$ receptor in the isolated guinea pig colon as a marker, independent of the Bezold-Jarisch reflex [A. S. Paintal et al., *Physiol. Rev.*, 53, 159 (1973)] which is conventionally used as a marker of the 5-HT$_3$ receptor agonistic activity, hence resulting in the accomplishment of the present invention.

Though a 2-aminoindenothiazole derivative having an antiulcer activity disclosed in JP-A-62-252780 (the term "JP-A" as used herein means an "unexamined published Japanese patent application") and a 2-amino condensed thiazole derivative having a muscarine receptor agonistic activity disclosed in JP-A-63-243080 have been known as condensed thiazole derivatives, the compounds of the present invention are novel compounds whose structure and activity are completely different from that of these compounds.

The condensed thiazole derivatives represented by the following general formula (I) or pharmaceutically acceptable salts thereof are characterized in that they have a high affinity for the 5-HT$_3$ receptor and show contractile effects in the isolated guinea pig colon used as the marker of a 5-HT$_3$ receptor agonistic activity.

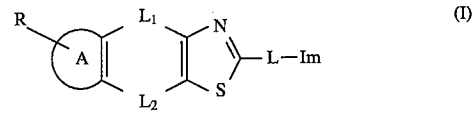

(Symbols in the above formula mean;

R: a hydrogen atom, a halogen atom, a hydroxyl group, a lower alkoxy group, a carboxy group, a lower alkoxycarbonyl group, a nitro group, an amino group, a cyano group or a protected hydroxyl group, Ⓐ: a phenyl ring or a naphthalene ring, L$_1$ and L$_2$: one is a direct bond and the other is
  a) a straight- or branched-lower alkylene group which may contain an interrupting oxygen or sulfur atom therein,
  b) an oxygen atom or a sulfur atom, or
  c) a lower alkenylene group, L: a direct bond or a straight- or branched-lower alkylene group, Im: a group represented by a formula

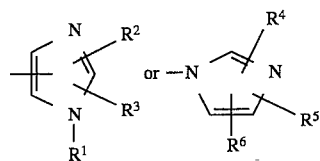

R$^1$, R$^2$ and R$^3$: the same or different from one another, each representing a hydrogen atom or a lower alkyl group, R$^4$, R$^5$ and R$^6$: the same or different from one another, each representing a hydrogen atom or a lower alkyl group.)

Accordingly, an object of the present invention is to provide the condensed thiazole derivatives represented by the above general formula (I) and pharmaceutically acceptable salts thereof.

Another object of the present invention is to provide a pharmaceutical composition which comprises the condensed thiazole derivative (I) described above or a pharmaceutically acceptable salt thereof and a pharmaceutically acceptable carrier.

Further object of the present invention is to provide a process for the production of the above-mentioned derivatives (I) or pharmaceutically acceptable salts thereof.

The compounds of the present invention are described in detail in the following.

Unless otherwise noted, the term "lower" in the definition of the general formula of this specification means a straight or branched carbon chain having 1 to 6 carbon atoms.

In consequence, illustrative examples of the "lower alkyl group" include methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2- trimethylpropyl, 1,2,2-trimethylpropyl, 1-ethyl-1-methylpropyl, 1-ethyl-2-methylpropyl and the like. Of these groups, $C_1$–$C_4$ alkyl groups, especially $C_1$–$C_3$ alkyl groups, are preferred.

Illustrative examples of the "lower alkoxy group" include methoxy, ethoxy, propoxy, isopropoxy, butoxy, isobutoxy, sec-butoxy, tert-butoxy, pentyloxy (amyloxy), isopentyloxy, tert-pentyloxy, neopentyloxy, 2-methylbutoxy, 1,2-dimethylpropoxy, 1-ethylpropoxy, hexyloxy and the like, of which $C_1$–$C_4$ alkoxy groups, especially $C_1$–$C_2$ alkoxy groups, are preferred.

Illustrative examples of the "lower alkoxycarbonyl group" include ($C_1$–$C_6$ alkoxy)carbonyl groups such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl, tert-pentyloxycarbonyl, hexyloxycarbonyl and the like, of which ($C_1$–$C_4$ alkoxy)carbonyl groups, especially ($C_1$–$C_2$ alkoxy)carbonyl groups, are preferred.

Illustrative examples of the "straight- or branched-lower alkylene group" represented by L include methylene, ethylene, methylmethylene, trimethylene, 1-methylethylene, 2-methylethylene, tetramethylene, 1-methyltrimethylene, 2-methyltrimethylene, 3-methyltrimethylene, 1-ethylethylene, 2-ethylethylene, 1,2-dimethylethylene, propylmethylene, pentamethylene, 1-methyltetramethylene, 2-methyltetramethylene, 3-methyltetramethylene, 4-methyltetramethylene, 1-ethyltrimethylene, 2-ethyltrimethylene, 3-ethyltrimethylene, 1,1-dimethyltrimethylene, 2,2-dimethyltrimethylene, 3,3-dimethyltrimethylene, hexamethylene, 1-methylpentamethylene, 2-methylpentamethylene, 3-methylpentamethylene, 4-methylpentamethylene, 5-methylpentamethylene, 1,1-dimethyltetramethylene, 4,4-dimethyltetramethylene and the like, of which straight or branched $C_1$–$C_4$ alkylene groups, especially straight or branched $C_1$–$C_3$ alkylene groups, are preferred.

The "straight- or branched-lower alkylene group which may contain an interrupting oxygen or sulfur atom therein" represented by either one of $L_1$ and $L_2$ includes "lower alkylene group which contains an interrupting oxygen or sulfur atom therein" and "lower alkylene group", and examples of the lower alkylene group include those illustrated above, preferably straight or branched $C_1$–$C_4$ alkylene groups, more preferably straight or branched $C_1$–$C_3$ alkylene groups which contains an interrupting oxygen or sulfur atom therein. Also, illustrative examples of the lower alkylene group which contains an interrupting oxygen or sulfur atom therein include all groups represented by a formula —$L_3$—Y—$L_4$— (wherein each of $L_3$ and $L_4$ is a direct bond or a straight or branched $C_1$–$C_6$ alkylene group, $L_3$ and $L_4$ have 1 to 6 carbon atoms in total, and Y is an oxygen atom or a sulfur atom), particularly preferred examples including an oxymethylene group (—O—$CH_2$—), a methyleneoxy group (—$CH_2$—O—), a thiomethylene group (—S—$CH_2$—), a methylenethio group (—$CH_2$—S—), a 1-oxatrimethylene group (—O—$CH_2CH_2$—, replacement nomenclature hereinafter), a 2-oxatrimethylene group (—$CH_2$—O—$CH_2$—), a 3-oxatrimethylene group (—$CH_2CH_2$—O—), a 2-methyl-1-oxaethylene group

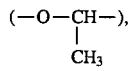

a 1-methyl-2-oxaethylene group

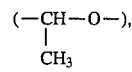

a 1-thiatrimethylene group (—S—$CH_2CH_2$—), a 2-thiatrimethylene group (—$CH_2$—S—$CH_2$—), a 3-thiatrimethylene group (—$CH_2CH_2$—S—), a 2-methyl-1-thiaethylene group

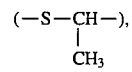

and a 1-methyl-2-thiaethylene group (—CH—S—).

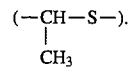

Illustrative examples of the "lower alkenylene group" represented by the other one of $L_1$ and $L_2$ include straight or branched $C_2$–$C_6$ alkenylene groups such as vinylene, propenylene, 2-propenylene, 1-methylvinylene, 2-methylvinylene, 1-butenylene, 2-butenylene, 3-butenylene, 1,3-butadienylene, 1-methylpropenylene, 2-methylpropenylene, 3-methylpropenylene, 1-methyl-2-propenylene, 2-methyl-2-propenylene, 3-methyl-2-propenylene, 1-ethylvinylene, 2-ethylvinylene, 1-propylvinylene, 2-propylvinylene, 1-isopropylvinylene, 2-isopropylvinylene and the like, of which those having $C_2$–$C_4$ alkenylene groups as the ring-constituting alkenylene chain, especially having $C_2$ alkenylene groups as the ring-constituting alkenylene chain, are preferred.

Illustrative examples of the "halogen atom" include a fluorine atom, a chlorine atom, a bromine atom and an iodine atom.

Illustrative examples of the "protecting group for the hydroxyl group" include benzyl, tert-butyl, acetyl, trifluoroacetyl, benzoyl, benzyloxycarbonyl and the like.

The compound (I) of the present invention forms acid additional salts. It also forms a salt with a base in some cases depending on the type of its substituent. Pharmaceutically acceptable salts of the compound (I) are also included in the present invention, and illustrative examples of these salts include acid addition salts with mineral acids such as hydrochloric acid, hydrobromic acid, hydroiodic acid, sulfuric acid, nitric acid, phosphoric acid and the like or with organic acids such as formic acid, acetic acid, propionic acid, oxalic acid, malonic acid, succinic acid, fumaric acid, maleic acid, lactic acid, malic acid, tartaric acid, citric acid, carbonic acid, methanesulfonic acid, ethanesulfonic acid, aspartic acid, glutamic acid and the like, salts with inorganic bases such as potassium, sodium, magnesium, calcium and the like or with organic bases such as trimethylamine, triethylamine, cyclohexylamine, monoethanolamine, diethanolamine, triethanolamine, arginine, lysine and the like, and ammonium salt.

Due to the presence of imidazole ring, 1H and 3H tautomers are present with respect to the compounds of the present invention. Also, it may contain an asymmetric carbon atom in some cases depending on the type of groups. Each single isomer isolated from a mixture of various isomers or a mixture thereof are also included in the present invention.

In addition, the compounds of the present invention are isolated in some cases as its hydrate, solvated substance or polymorphic form, and these substances are also included in the present invention.

Particularly preferred examples of the compounds of the present invention are those in which the A ring is a phenyl ring, $L_1$ is a direct bond and $L_2$ is a straight- or branched-lower alkylene group or a lower alkenylene group. Of these, optimum compounds are illustrated below.

(1) 2-(4-Imidazolylmethyl)-8H-indeno[1,2-d]thiazole or its pharmaceutically acceptable salts.

(2) 2-(4-Imidazolylmethyl)-4,5-dihydronaphtho[1,2-d]thiazole or its pharmaceutically acceptable salts.

(Production method)

The compounds (I) of the present invention and their pharmaceutically acceptable salts can be produced by application of various synthetic methods taking advantage of the characteristics of their basic chemical structure or substituent. From the viewpoint of production techniques, it is effective in some cases to protect an amino group (including an imidazole nitrogen), a carboxy group and a hydroxyl group of the compound of the present invention with appropriate protecting groups, namely functional groups which can be easily deprotected into an amino group (including an imidazole nitrogen), a carboxy group and a hydroxyl group, respectively. Examples of such protecting groups include those which are reported by Greene and Wuts in *Protective Groups in Organic Synthesis,* 2nd edition, and these groups may be used optionally depending on the reaction conditions. In addition to these protecting groups, other functional groups which can be converted easily into an amino group, a carboxy group and a hydroxyl group can also be used as the protecting groups.

The following illustrate typical processes for the production of the compounds (I) of the present invention and their salts.

Production process 1 (cyclization reaction)

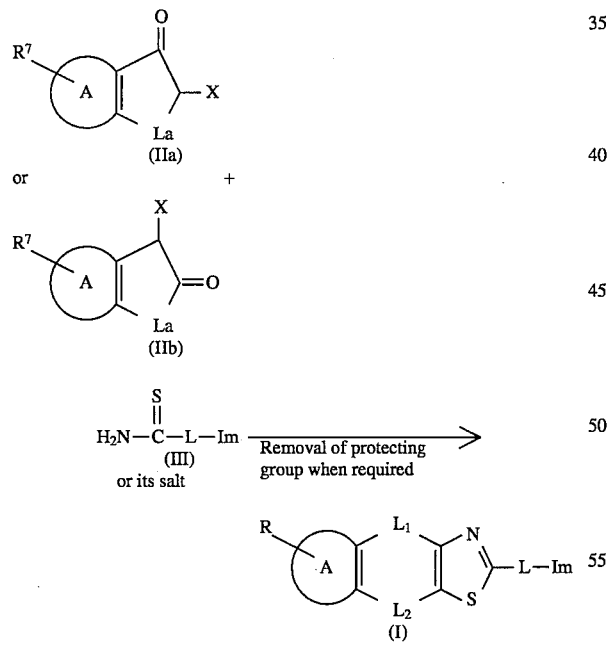

(In the reaction formula, (A), $L_1$, $L_2$, L and Im are as defined in the foregoing, $R^7$ is the same group as R which may have a protecting group, La is a) a straight- or branched-lower alkylene group which may contain an interrupting oxygen or sulfur atom therein, b) an oxygen atom or a sulfur atom or c) a lower alkenylene group, and X is a halogen atom.)

The compounds (I) of the present invention can be produced by a reaction of an α-halogenoketone derivative represented by the general formula (IIa) or (IIb) with a thioamide derivative represented by the general formula (III) or a salt thereof to effect cyclization and then eliminating the protecting groups when required.

Herein, examples of the halogen atom represented by X include an iodine atom, a bromine atom, a chlorine atom and the like.

It is advantageous to carry out the reaction in an inert organic solvent such as alcoholic solvents (e.g., isopropanol, methanol, ethanol or the like) or an aqueous alcoholic solvent at room temperature or with heating, preferably with heating under reflux, using an equimolar amounts of (IIa) or (IIb) and (III) or using one of them in an excess molar ratio.

The elimination of the protecting group varies depending on the type of the protecting group; for example, catalytic reduction may be used suitably when the protecting group for the amino group is a substituted or unsubstituted benzyloxycarbonyl group or the like, or an acid treatment with, for example, hydrobromic acid/acetic acid, hydrobromic acid/trifluoroacetic acid, hydrofluoric acid or the like may be employed in some cases. In the case of other urethane type protecting groups such as tert-butoxycarbonyl group and the like, it is advantageous to eliminate the protecting group by acid treatment with hydrobromic acid/acetic acid, trifluoroacetic acid, hydrochloric acid, hydrochloric acid/acetic acid, hydrochloric acid/dioxane or the like.

With regard to the protecting group for the carboxy group, a methyl group and an ethyl group can be removed easily by saponification, and a benzyl group and various kinds of substituted benzyl groups can be removed by catalytic reduction or saponification, a tert-butyl group can be removed by the above acid treatment and a trimethylsilyl group can be removed by its contact with water.

With regard to the protecting groups for the hydroxy group, most of them can be removed by their treatment with sodium/liquid ammonia or hydrofluoric acid, some of them (for example, O-benzyl and O-benzyloxycarbonyl) can be removed by catalytic reduction, and acyl protecting groups such as a benzoyl group, an acetyl group and the like can be removed by hydrolysis in the presence of an acid or an alkali.

These treatments can be carried out in the usual way.

Production process 2 (C-alkylation or N-alkylation of the imidazole ring)

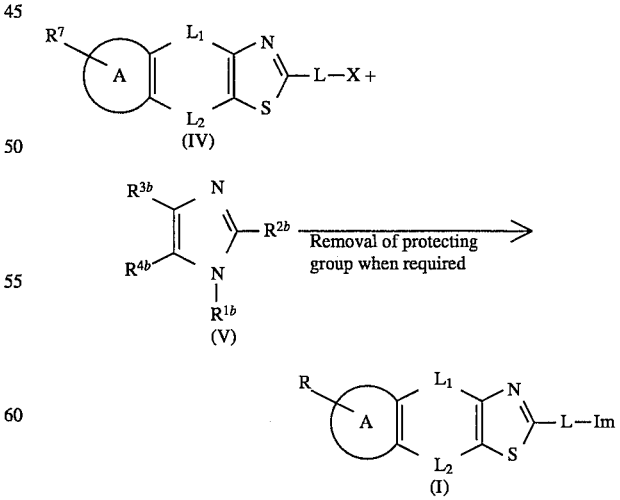

(In the reaction formula, R, $R^7$, (A), $L_1$, $L_2$, L, X and Im are as defined in the foregoing, $R^{1b}$ is a hydrogen atom, a lower alkyl group or a protecting group of the imidazole nitrogen, and $R^{2b}$, $R^{3b}$ and $R^{4b}$ are the same or different from one another and each represents a hydrogen atom or a lower alkyl group, with the proviso that at least one of $R^{1b}$ or $R^{4b}$ is a hydrogen atom.)

The compounds (I) of the present invention and their salts can be produced by a reaction of a halogenoalkyl-substituted condensed thiazole derivative represented by the general formula (IV), which may have a protecting group, with an imidazole derivative represented by the general formula (V), which may have a protecting group for an imidazole nitrogen atom, and then eliminating the protecting group when required.

It is advantageous to carry out the reaction using equimolar amounts of the compounds (IV) and (V) or using one of them in an excess molar ratio, at the temperature of from cold temperature to heated temperature or with heating under reflux in an inert solvent such as dimethylformamide, dimethylsulfoxide, ether, tetrahydrofuran, dioxane, acetone, methyl ethyl ketone, methanol, ethanol, methylene chloride, dichloroethane, chloroform or the like, if necessary in the presence of a base such as pyridine, picoline, dimethylaniline, N-methylmorpholine, trimethylamine, triethylamine, sodium hydride, potassium carbonate, sodium carbonate, sodium bicarbonate, sodium hydroxide, potassium hydroxide or the like.

Especially, in the case of a C-alkylation reaction, it is possible to carry out the reaction of the compound (IV) with an alkali metal salt of the compound (V) at a temperature within the range of from a low temperature, e.g., −100° C., to room temperature, in an inert aprotic solvent such as ether, tetrahydrofuran, dioxane or the like, if necessary by the addition of hexamethylphosphoramide, hexamethylphosphorous triamide, tetramethylethylenediamine or the like, and using a required amount of a base such as n-butyllithium, sec-butyllithium, t-butyllithium, lithium diisopropylamide, potassium t-butoxide, sodium hydride or the like.

Elimination of the protecting groups can easily proceed in the same manner as the case of the production process 1, for example, by an acid treatment or by catalytic reduction when a trityl group or a benzhydryl group is used as the protecting group for the imidazole nitrogen. Hydrochloric acid, acetic acid, trifluoroacetic acid or a mixture thereof with dioxane may be used as the acid, and the catalytic reduction may be carried out in the presence of a catalyst such as palladium carbon, palladium oxide, palladium hydroxide, platinum, platinum oxide, Raney nickel or the like. Production process 3 (mutual conversion between desired compounds)

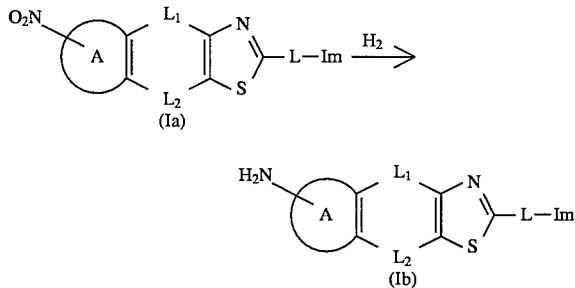

(In the reaction formula, Ⓐ, $L_1$, $L_2$, L and Im are as defined in the foregoing.)

The compounds of the present invention whose R is amino group, i.e., the compound (Ib), can be produced by reducing the corresponding nitro compound (Ia).

This reaction can be effected by applying conventional methods for the reduction of aromatic nitro compounds, particularly, by a method in which catalytic hydrogenation is carried out in an inert solvent such as an alcoholic solvent (e.g., methanol, ethanol, isopropanol or the like) or an aqueous alcohol in the presence of a catalyst such as Raney nickel, palladium carbon, platinum, platinum black or the like.

The compounds (I) of the present invention produced in these manners are isolated and purified as the free compound or in the form of their salt, hydrate, solvated substance or the like. In this instance, pharmaceutically acceptable salts of the compound (I) of the present invention can also be produced by subjecting them to the conventional salt forming reaction.

Isolation and purification of the compound are carried out by employing conventional chemical techniques such as extraction, fractional crystallization, recrystallization, various fractional chromatography and the like.

Tautomers can be separated taking advantage of the difference in physicochemical properties between the isomers.

Racemic compounds can be led into a stereochemically pure isomer by the use of an appropriate starting material or in accordance with a conventional resolution method [for example, a method in which a compound is converted into a diastereomeric salt with a usual optically active acid (tartaric acid or the like) and then subjected to optical resolution]. In addition, a diastereomer mixture can be separated in the usual manner, for example, by fractional crystallization, chromatography or the like.

INDUSTRIAL APPLICABILITY

The compounds of the present invention show excellent 5-$HT_3$ receptor agonistic activity, especially, in terms of the contractile effects in the isolated guinea pig colon. The following description illustrates such activities together with their measuring methods.

1) 5-$HT_3$ receptor agonistic activity

Distal colons were excised from male Hartley guinea pigs (500 to 800 g) to prepare strips of about 20 mm.

Each strip was longitudinally suspended in a Magnus tube, and contractile response was isometrically measured.

5-HT caused a dose-dependent contraction within its concentration range of 0.1 to 30 μM and showed the maximal response at 10 to 30 μM (the action of 5-HT is mediated via the 5-$HT_3$ receptor: *J. Pharmacol. Exp. Ther.*, 259, 15–21, 1991).

Activity of each compound is expressed by relative value in comparison with the activity of 5-HT in each specimen.

The max. response is indicated as percentage of the maximal response by each compound when the maximal contraction by 5-HT is defined as 100%.

The relative potency is shown by relative $EC_{50}$ value for each compound based on the standard value (1) of that of 5-HT.

$$\left(\text{Relative potency} = \frac{EC_{50} \text{ value for 5-HT}}{EC_{50} \text{ value for compound}}\right)$$

|  | Max. response | Relative potency |
|---|---|---|
| Compound of Example 1 | 89.9 | 26 |
| Compound of Example 3 | 80.3 | 45 |
| Compound of Example 4 | 50.0 | 1–3 |
| Compound of Example 10 | 60.9 | 2–3 |
| Compound of Example 15 | 42.6 | 5 |
| Compound of Example 30 | 78.2 | 2 |

(1) The compounds of the present invention showed contractile effects in the isolated guinea pig colon in a concentration-dependent fashion under a concentration of 300 μM.

(2) The contractile effects in the isolated guinea pig colon to the compounds of the present invention was antagonized by 0.3 μM of a compound which is a 5-HT$_3$ receptor antagonist described in Example 44 of JP-A-3-223278.

2) Receptor binding experiment

The compound of Example 1 showed high affinity for the 5-HT$_3$ receptor in the receptor binding experiment.

On the basis of the above results, it was confirmed that the compounds of the present invention exhibit a strong 5-HT$_3$ receptor agonist.

Preferred examples of the compound of the present invention are compounds which exert the above-mentioned functions but hardly show the 5-HT$_3$ receptor agonistic activity when measured using the Bezold-Jarisch reflex (S. Paintal et al., *Physiol. Rev.*, 53, 159 (1973)) which is a conventional index of the 5-HT$_3$ receptor agonistic activity.

In this connection, the present invention also includes certain compounds which have 5-HT$_3$ receptor antagonistic activity, and such compounds should be regarded as another embodiment of the present invention. These compounds seem to be applicable to the medicinal use disclosed by the present inventors in relation to tetrahydrobenzimidazole derivatives, for example, in JP-A-3-223278, such as inhibition of emesis caused by carcinostatic agents such as cisplatin and the like or radiation exposure, and prevention and treatment of migraine headache, complex headache, trigeminal neuralgia, anxiety symptoms, gastrointestinal motility disorder, peptic ulcer, irritable bowel syndrome and the like.

The compounds (I) of the present invention or their salt, solvate or hydrate exerts specific action upon neuronal 5-HT$_3$ receptor located in myenteric plexus and, therefore, are useful for the treatment of gastrointestinal disorders such as senile, atonic or proctogenic constipation, acute or chronic gastritis, gastric or duodenal ulcer, gastrointestinal neurosis, gastroptosis, reflux esophagitis, gastrointestinal motility disorders caused by diseases such diabetes and the like, gastrointestinal function insufficiency after anesthetic operation, gastric retention, dyspepsia, meteorism and the like. It can be used also for the treatment of pancreatic insufficiency-induced diseases such as fat absorption insufficiency and the like.

In addition, the compounds of the present invention are also useful for the treatment of certain symptoms such as mental disorders (schizophrenia and depression, for example), anxiety, memory disturbance and the like.

Being low in toxicity, the compounds of the present invention are suitable for use as medicines. For example, each of the compounds of Examples 1 and 3 do not cause serious grave side effects when they are administered in a dose of 100 mg/kg i.v. to ICR male mice (8 to 9 weeks of age, 30 to 40 g, n=5 to 6).

The compounds (I) of the present invention and their pharmaceutically acceptable salts and the like are made into tablets, powders, fine granules, capsules, pills, solutions, injections, suppositories, ointments, plasters and the like, making use of conventionally used pharmaceutically acceptable carriers, excipients and other additives, and administered orally (including sublingual administration) or parenterally.

The carriers and excipients for use in the drug preparation are solid or liquid non-toxic substances for medicinal use. Their illustrative examples include lactose, magnesium stearate, starch, talc, gelatin, agar, pectin, acacia, olive oil, sesame oil, cacao butter, ethylene glycol and other conventionally used substances.

Clinical dose of the compound of the present invention is optionally decided taking symptoms, body weight, age, sex and the like of each patient into consideration, which is generally 1 to 100 mg per day per adult in the case of oral administration and the daily dose may be divided into 1 to several doses per day.

BEST MODE OF CARRYING OUT THE INVENTION

Next, an example of the preparation of a pharmaceutical preparation making use of the compound of the present invention is described.

| Formulation Example (tablets) | |
|---|---|
| composition | 20 mg tablet |
| inventive compound | 20 mg |
| lactose | 75 |
| corn starch | 16 |
| hydroxypropylcellulose | 4.5 |
| carboxymethylcellulose calcium | 8.8 |
| magnesium stearate | 0.7 |
| total | 120 mg |

20 mg Tablet

A 100 g portion of the compound of the present invention was uniformly mixed with 375 g of lactose and 80 g of corn starch using a fluidized bed granulation coating apparatus. To this was sprayed 225 g of 10% hydroxypropylcellulose solution to effect granulation. After drying, granules were passed through a 20 mesh screen, mixed with 19 g of carboxymethylcellulose calcium and 3.5 g of magnesium stearate and then made into tablets, each weighing 120 mg, by a rotary tabletting machine using a 7 mm×8.4 R punch.

EXAMPLES

The following examples are provided to illustrate the present invention further in detail. In this connection, novel compounds are included in the starting materials of the present invention. Processes for the production of the starting materials are shown in the following Reference Examples.

Reference Example 1 a) 373 mg of sodium hydride (60%) was added to 5 ml of dimethylformamide, and a solution of 1.0 g of 4-cyanomethylimidazole in 10 ml of dimethylformamide was added dropwise to the resulting suspension. After 1 hour of stirring at room temperature, to the solution was added 1.9 ml of (2-chloromethoxyethyl)trimethylsilane and stirred at room temperature for 2 hours. The reaction solution was mixed with water and chloroform, and the resulting organic layer was collected and dried over anhydrous sodium sulfate, followed by evaporation of the solvent. The residue was subjected to silica gel column chromatography eluted with hexane-ethyl acetate (1:1) to obtain 1.128 g of 4-cyanomethyl-1-trimethylsilylethoxymethylimidazole and 0.362 g of 5-cyanomethyl-1-trimethylsilylethoxymethylimidazole.

4-Cyanomethyl-1-trimethylsilylethoxymethylimidazole

Nuclear magnetic resonance spectrum (CDCl$_3$, TMS internal standard) δ: 0.29 (2H, t), 3.50 (2H, t), 3.72 (2H, s), 5.25 (2H, s), 7.08 (1H, s), 7.56 (1H, s)

5-Cyanomethyl-1-trimethylsilylethoxymethylimidazole

Nuclear magnetic resonance spectrum (CDCl$_3$, TMS internal standard) δ: 0.93 (2H, t), 3.49 (2H, t), 3.81 (2H, s), 5.33 (2H, s), 7.10 (1H, s), 7.58 (1H, s)

b) 0.16 ml of methyl iodide was added to 600 mg of 4-cyanomethyl-1-trimethylsilylethoxymethylimidazole obtained in the above step a), and the mixture was heated in a sealed tube at 60° C. for 24 hours. After addition of diethyl ether to the reaction solution and removing the supernatant fluid, the residue was dried under a reduced pressure to obtain 82 mg of 4-cyanomethyl-3-methyl-1-trimethylsilylethoxymethylimidazolium iodide.

Nuclear magnetic resonance spectrum (DMSO-d$_6$, TMS internal standard) δ: 0.90 (2H, t), 3.62 (2H, t), 3.83 (2H, s), 4.35 (3H, s), 5.56 (2H, s), 7.90 (1H, s), 9.42 (1H, s)

c) 157 mg of 4-cyanomethyl-3-methyl-1-trimethylsilylethoxymethylimidazolium iodide obtained in the above step b) was dissolved in 5 ml of ethanol, mixed with 5 ml of 1N hydrochloric acid and then heated at 60° C. for 6 hours. The reaction solution was mixed with a 1N aqueous sodium hydroxide solution and diethyl ether, and the resulting organic layer was collected, washed with water and a saturated aqueous solution of sodium chloride and then dried over anhydrous sodium sulfate, followed by evaporation of the solvent. The residue was subjected to alumina column chromatography eluted with dichloromethane-methanol (30:1) to obtain 15 mg of 5-cyanomethyl-1-methylimidazole.

Mass spectrometry value (m/z): 112 (M$^+$)

Nuclear magnetic resonance spectrum (CDCl$_3$, TMS internal standard) δ: 3.70 (5H, s), 6.90 (1H, s), 7.37 (1H, s)

d) Using 500 mg of 5-cyanomethyl-1-trimethylsilylethoxymethylimidazole obtained in the above step a), 75 mg of 4-cyanomethyl-1-methyl-3-trimethylethoxymethylimidazolium iodide was obtained by the same manner as the procedure in the above step b).

Nuclear magnetic resonance spectrum (DMSO-d$_6$, TMS internal standard) δ: 0.90 (2H, t), 3.62 (2H, t), 3.83 (2H, s), 3.51 (3H, s), 5.56 (2H, s), 7.92 (1H, s), 9.40 (1H, s)

e) 200 mg of 4-cyanomethyl-1-methyl-3-trimethylethoxymethylimidazolium iodide obtained in the above step d) was treated in the same manner as the procedure of step c) to obtain 20 mg of 4-cyanomethyl-1-methylimidazole.

Mass spectrometry value (m/z): 112 (M$^+$)

Nuclear magnetic resonance spectrum (CDCl$_3$, TMS internal standard) δ: 3.67 (3H, s), 3.72 (2H, s), 7.00 (1H, s), 7.47 (1H, s)

Reference Example 2

1.3 g of sodium hydride (60%) was added to 10 ml of tetrahydrofuran, and a solution of 2.0 g of imidazole in 10 ml of tetrahydrofuran was added dropwise to the resulting suspension. After 2 hours of stirring at 0° C., the solution was mixed with 1.86 ml of chloroacetonitrile and stirred at room temperature for 3 hours. To the reaction solution was added water and chloroform, and the organic layer was collected and dried over anhydrous sodium sulfate, followed by evaporation of the solvent. The residue was subjected to alumina column chromatography eluted with dichloromethane-methanol (200:1) to obtain 1.043 g of 1-cyanomethylimidazole.

Mass spectrometry value (m/z): 107 (M$^+$+1)

Nuclear magnetic resonance spectrum (CDCl$_3$, TMS internal standard) δ: 4.95 (2H, s), 7.06 (1H, d), 7.09 (1H, d), 7.57 (1H, s)

Reference Example 3

Using 2.35 ml of 3-chloropropionitrile, 2.0 g of imidazole and 1.3 g of sodium hydride (60%), 3.2 g of 1-(2-cyanoethyl)imidazole was obtained by the same manner as the procedure of Reference Example 2.

Mass spectrometry value (m/z): 121 (M$^+$)

Nuclear magnetic resonance spectrum (CDCl$_3$, TMS internal standard) δ: 2.81 (2H, t), 4.25 (2H, t), 7.06 (2H, d), 7.55 (1H, s)

Reference Example 4

Using 1.75 g of 4-chlorobutylonitrile, 805 mg of imidazole and 566 mg of sodium hydride (60%), 1.15 g of 1-(3-cyanopropyl) imidazole was obtained by the same manner as the procedure of the Reference Example 2.

Nuclear magnetic resonance spectrum (CDCl$_3$, TMS internal standard) 67 : 2.05–2.42 (4H, m), 4.12 (2H, t), 6.96 (1H, s), 7.08 (1H, s), 7.51 (1H, s)

Reference Example 5 a) 1.5 g of 2-imidazole carboxaldehyde was dissolved in 20 ml of dimethylformamide, 2.18 ml of triethylamine and 4.3 g of triphenylmethyl chloride were added to the above solution, and then the resulting mixture was stirred at room temperature for 24 hours. A saturated sodium bicarbonate aqueous solution and chloroform were added to the reaction solution, and the resulting organic layer was collected, washed with a saturated aqueous sodium chloride solution and then dried over anhydrous sodium sulfate, followed by evaporation of the solvent. The residue was subjected to silica gel chromatography eluted with dichloromethane-methanol (50:1) to obtain 4.717 g of 1-triphenylmethyl-2-imidazole carboxaldehyde.

Mass spectrometry value (m/z): 339 (M$^+$+1)

Nuclear magnetic resonance spectrum (CDCl$_3$, TMS internal standard) δ: 7.02–7.51 (17H, m), 9.23 (1H, s)

b) 4.717 g of 1-triphenylmethyl-2-imidazole carboxaldehyde obtained in the above step a) was dissolved in 50 ml of methanol-tetrahydrofuran (1:1), 526 mg of sodium borohydride was added to the solution at −78° C. After stirring at −78° C. for 1 hour, a saturated aqueous ammonium chloride solution and dichloromethane were added to the resultant solution. The resulting organic layer was collected, washed with water and a saturated aqueous sodium chloride solution and then dried over anhydrous sodium sulfate, followed by evaporation of the solvent. The residue was washed with diethyl ether to obtain 1.691 g of 2-hydroxymethyl-1-triphenylmethylimidazole.

Mass spectrometry value (m/z): 341 (M$^+$+1)

Nuclear magnetic resonance spectrum (CDCl$_3$, TMS internal standard) δ: 3.66 (2H, s), 6.79 (1H, d), 7.00–7.41 (16H, m)

c) With cooling in an ice bath, 6.2 ml of thionyl chloride was added to 7.728 g of 2-hydroxymethyl-1-triphenylmethylimidazole obtained in the above step b), and the mixture was warmed to room temperature and stirred for 30 minutes.

By evaporation of the solvent, 3.466 g of 2-chloromethylimidazole hydrochloride was obtained.

Nuclear magnetic resonance spectrum (DMSO-$d_6$, TMS internal standard) δ: 5.05 (2H, s), 7.70 (2H, s)

d) With cooling in an ice bath, 7.5 g of potassium cyanide was dissolved in 26 ml of water to which was subsequently added dropwise a solution of 3.446 g of 2-chloromethylimidazole hydrochloride obtained in the above step c) in 130 ml of ethanol, for 1.5 hours, followed by 2.5 hours of stirring at room temperature. The reaction solution was filtered, a saturated aqueous sodium carbonate solution was added to the resulting filtrate and then the solvent was removed by evaporation. The residue was extracted with ethyl acetate, the extract was filtered and then the solvent was removed by evaporation. The residue was subjected to alumina column chromatography eluted with dichloromethane-methanol (50:1) to obtain 1.218 g of 2-cyanomethylimidazole.

Mass spectrometry value (m/z): 108 ($M^+$+1)

Nuclear magnetic resonance spectrum (DMSO-$d_6$, TMS internal standard) δ: 4.07 (2H, s), 7.33 (2H, s)

Reference Example 6

450 mg of sodium hydride (60%) was added to 5 ml of dimethylformamide, and a solution of 1.0 g of 4-cyanomethylimidazole in 10 ml of dimethylformamide was added dropwise to the resulting suspension. After 1 hour of stirring at room temperature, 0.94 ml of 2-propyl iodide was added to the resulting solution and stirred at room temperature for 2 hours. To the reaction solution was added water and chloroform, and the resulting organic layer was collected and dried over anhydrous sodium sulfate, followed by evaporation of the solvent. The residue was subjected to silica gel column chromatography eluted with chloroform-methanol (30:1) to obtain 500 mg of 4-cyanomethyl-1-(2-propyl)imidazole.

Nuclear magnetic resonance spectrum (CDCl$_3$, TMS internal standard) δ: 1.32 (6H, d), 3.54 (2H, s), 4.20 (1H, m), 6.83 (1H, s), 7.82 (1H, s)

Reference Example 7

To 660 mg of 5-cyanomethyl-1-methylimidazole obtained in Reference Example 1c) was added 10 ml of 4N hydrochloric acid-ethyl acetate solution, and then 0.92 ml of O,O-diethyl dithiophosphate, and the mixture was stirred at room temperature for 18 hours. The resulting solid was collected by filtration, washed with ethyl acetate and then diethyl ether, and dried under a reduced pressure to obtain 966 mg of (1-methyl-5-imidazolyl) thioacetamide hydrochloride.

Mass spectrometry value (m/z): 156 ($M^+$+1)

Reference Example 8

Using 185 mg of 4-cyanomethyl-1-methylimidazole obtained in Reference Example 1e), 282 mg of (1-methyl-4-imidazolyl) thioacetamide hydrochloride was obtained by the same manner as described in Reference Example 7.

Mass spectrometry value (m/z): 156 ($M^+$+1)

Nuclear magnetic resonance spectrum (DMSO-$d_6$, TMS internal standard) δ: 3.78 (3H, s), 3.84 (2H, s), 7.55 (2H, s), 9.85 (2H, br)

Reference Example 9

Using 0.88 g of 1-cyanomethylimidazole obtained in Reference Example 2, 1.309 g of 1-imidazolylthioacetamide hydrochloride was obtained by the same manner as described in Reference Example 7.

Mass spectrometry value (m/z): 142 ($M^+$+1)

Nuclear magnetic resonance spectrum (DMSO-$d_6$, TMS internal standard) δ: 5.23 (2H, s), 7.64 (1H, d), 7.68 (1H, d), 9.14 (1H, s), 9.98 (2H, br)

Reference Example 10

Using 3.2 g of 1-(2-cyanoethyl)imidazole obtained in Reference Example 3, 3.219 g of 3-(1-imidazolyl)-propanethioamide hydrochloride was obtained by the same manner as described in Reference Example 7.

Mass spectrometry value (m/z): 155 ($M^+$)

Nuclear magnetic resonance spectrum (DMSO-$d_6$, TMS internal standard) δ: 3.19 (2H, t), 4.58 (2H, t), 7.06 (2H, d), 7.55 (1H, s), 9.98 (2H, br)

Reference Example 11

Using 1.15 g of 1-(3-cyanopropyl)imidazole obtained in Reference Example 4, 1.96 g of 4-(1-imidazolyl)butanethioamide hydrochloride was obtained by the same manner as described in Reference Example 7.

Mass spectrometry value (m/z): 169 ($M^+$)

Reference Example 12

Using 1.208 g of 2-cyanomethylimidazole obtained in Reference Example 5d), 1.005 g of 2-imidazolylthioacetamide hydrochloride was obtained by the same manner as described in Reference Example 7.

Mass spectrometry value (m/z): 142 ($M^+$+1)

Nuclear magnetic resonance spectrum (DMSO-$d_6$, TMS internal standard) δ: 4.31 (2H, s), 7.56 (2H, s), 9.95 (2H, br)

Reference Example 13

Using 850 mg of 4-cyanomethyl-1-(2-propyl)imidazole obtained in Reference Example 6, 905 mg of [1-(2-propyl)-4-imidazoyl] thioacetamide hydrochloride was obtained by the same manner as described in Reference Example 7.

Mass spectrometry value (m/z): 184 ($M^+$+1)

Nuclear magnetic resonance spectrum (DMSO-$d_6$, TMS internal standard) δ: 1.47 (6H, d), 3.99 (2H, s), 4.63 (1H, m), 7.74 (1H, s), 9.18 (1H, s), 9.95 (2H, br)

Reference Example 14

Using 1.9 g of 4(5)-(1-cyanoethyl)-1-triphenylmethylimidazole, 2.0 g of 2-(4-imidazolyl)propanethioamide hydrochloride was obtained by the same manner as described in Reference Example 7.

Mass spectrometry value (m/z): 156 ($M^+$+1)

Example 1

0.34 g of 2-bromo-1-indanone and 0.26 g of 4-imidazolyl thioacetamide hydrochloride were dissolved in 7 ml of 2-propanol with heating, and the solution was heated for 30 minutes under reflux. After cooling the reaction solution, the precipitated crystals were collected by filtration and washed with ethyl acetate. The collected crystals were partitioned between chloroform and a saturated aqueous sodium bicarbonate solution, and the aqueous layer was extracted with chloroform several times. The combined chloroform layers were washed with a saturated aqueous sodium chloride solution and then dried over anhydrous magnesium sulfate. By evaporation of the solvent, 0.12 g (32%) of 2-(4-imidazolylmethyl)- 8H-indeno[1,2-d]thiazole was obtained. This free base was dissolved in methanol and mixed with 0.055 g of fumaric acid to effect crystallization. The resulting crude crystals were recrystallized from methanol-diethyl ether to obtain 0.10 g of fumarate.

Melting point: 202°–203° C. methanol-diethyl ether

Elemental analysis data (as $C_{14}H_{11}N_3S \cdot C_4H_4O_4$)

|  | C (%) | H (%) | N (%) | S (%) |
|---|---|---|---|---|
| calcd. | 58.53 | 4.09 | 11.38 | 8.68 |
| found | 58.37 | 4.21 | 11.25 | 8.69 |

Mass spectrometry value (m/z): 253 ($M^+$)

Nuclear magnetic resonance spectrum (DMSO-$d_6$, TMS internal standard) δ: 3.87 (2H, s), 4.34 (2H, s), 6.63 (2H, s), 7.07 (1H, s), 7.24 (1H, t), 7.36 (1H, t), 7.54 (1H, d), 7.63 (1H, d), 7.69 (1H, s)

Examples 2 to 27a

The following compounds were obtained by the same manner as described in Example 1.

Example 2

2-(4-Imidazolylmethyl) -4H-indeno[2,1-d]thiazole hemifumarate

Starting compounds: 1-bromo-2-indanone, 4-imidazolyl thioacetamide hydrochloride Melting point: 170°–172° C. ethanol-diethyl ether Elemental analysis data (as $C_{14}H_{11}N_3 \cdot 0.5\ C_4H_4O_4 \cdot 0.1\ H_2O$)

|  | C (%) | H (%) | N (%) | S (%) |
|---|---|---|---|---|
| calcd. | 61.37 | 4.25 | 13.42 | 10.24 |
| found | 61.13 | 4.27 | 13.06 | 10.12 |

Mass spectrometry value (m/z): 253 ($M^+$)

Nuclear magnetic resonance spectrum (DMSO-$d_6$, TMS internal standard) δ: 3.81 (2H, s), 4.32 (2H, s), 6.63 (1H, s), 7.1–7.8 (6H, m)

Example 3

2-(4-Imidazolylmethyl)-4,5-dihydronaphtho[1,2-d]thiazole fumarate

Starting compounds: 2-bromo-1-tetralone, 4-imidazolyl thioacetamide hydrochloride Melting point: 180°–182° C. methanol-diethyl ether Elemental analysis data (as $C_{15}H_{13}N_3S \cdot C_4H_4O_4 \cdot 0.1\ H_2O$)

|  | C (%) | H (%) | N (%) | S (%) |
|---|---|---|---|---|
| calcd. | 59.24 | 4.50 | 10.91 | 8.32 |
| found | 58.99 | 4.50 | 10.86 | 8.36 |

Mass spectrometry value (m/z): 267 ($M^+$)

Nuclear magnetic resonance spectrum (DMSO-$d_6$, TMS internal standard) δ: 2.95 (4H, s), 4.20 (2H, s), 6.71 (2H, s), 7.1–7.9 (6H, m)

Example 4

2-(4-Imidazolylmethyl)-5,6-dihydro-4H-benzo[6,7]-cyclohepto[1,2-d]thiazole fumarate Starting compounds: 2-bromo-1-benzosuberone, 4-imidazolyl thioacetamide hydrochloride Melting point: 149°–150° C. methanol-ethyl acetate Elemental analysis data (as $C_{16}H_{15}N_3S \cdot C_4H_4O_4 \cdot 0.25\ H_2O$)

|  | C (%) | H (%) | N (%) | S (%) |
|---|---|---|---|---|
| calcd. | 59.76 | 4.89 | 10.45 | 7.98 |
| found | 59.71 | 4.84 | 10.39 | 7.70 |

Mass spectrometry value (m/z): 281 ($M^+$)

Nuclear magnetic resonance spectrum (DMSO-$d_6$, TMS internal standard) δ: 2.01–2.08 (2H, m), 2.74–2.77 (2H, m), 2.94 (2H, t), 4.19 (2H, s), 6.63 (2H, s), 7.04 (1H, s), 7.19–7.30 (3H, m), 7.63 (1H, s), 7.99 (1H, d)

Example 5

2-(4-Imidazolylmethyl)-5-methyl-4,5-dihydronaphtho[1,2-d]-thiazole

Starting compounds: 2-bromo-4-methyl-1-tetralone, 4-imidazolyl thioacetamide hydrochloride Melting point: 184°–186° C. (dec.) ethyl acetate Elemental analysis data (as $C_{16}H_{15}N_3S \cdot 0.1\ H_2O$)

|  | C (%) | H (%) | N (%) | S (%) |
|---|---|---|---|---|
| calcd. | 67.86 | 5.46 | 14.84 | 11.32 |
| found | 67.90 | 5.43 | 14.80 | 11.37 |

Mass spectrometry value (m/z): 282 ($M^++1$)

Nuclear magnetic resonance spectrum (DMSO-$d_6$, TMS internal standard) δ: 1.20 (3H, d), 2.77 (1H, dd), 3.05–3.18 (2H, m), 4.23 (2H, s), 7.03 (1H, s), 7.21–7.29 (3H, m), 7.61 (1H, s), 7.78 (1H, dd), 11.99 (1H, brs)

Example 6

2-(4-Imidazolylmethyl)-4H-[1]benzopyrano[4,3-d]thiazole fumarate

Starting compounds: 3-bromo-4-chromanone, 4-imidazolyl thioacetamide hydrochloride Melting point: 180°–184° C. (dec.) methanol Elemental analysis data (as $C_{14}H_{11}N_3OS \cdot C_4H_4O_4 \cdot 0.1 H_2O$)

|  | C (%) | H (%) | N (%) | S (%) |
|---|---|---|---|---|
| calcd. | 55.84 | 3.96 | 10.85 | 8.28 |
| found | 55.77 | 3.92 | 10.74 | 8.12 |

Mass spectrometry value (m/z): 269 (M$^+$)

Nuclear magnetic resonance spectrum (DMSO-d$_6$, TMS internal standard ) δ: 4.28 (2H, s), 5.45 (2H, s), 6.63 (2H, s), 6.93 (1H, d), 7.03 (1H, t), 7.07 (1H, s), 7.20 (1H, t), 7.63–7.68 (2H, m)

Example 7

2-(4-Imidazolylmethyl)-4H-[1]benzothiopyrano[4,3-d]-thiazole

Starting compounds: 3-bromothiochroman-4-one, 4-imidazolyl thioacetamide hydrochloride Melting point: 199°–202° C. (dec.) methanol Elemental analysis data (as $C_{14}H_{11}N_3S_2 \cdot 0.2 H_2O$)

|  | C (%) | H (%) | N (%) | S (%) |
|---|---|---|---|---|
| calcd. | 58.19 | 3.98 | 14.54 | 22.19 |
| found | 58.29 | 3.97 | 14.47 | 21.93 |

Mass spectrometry value (m/z): 285 (M$^+$)

Nuclear magnetic resonance spectrum (CDCl$_3$, TMS internal standard) δ: 4.10 (2H, s), 4.35 (2H, s), 6.97 (2H, s), 7.17 (1H, dr), 7.23 (1H, dr), 7.32 (1H, dd), 7.64 (1H, s), 8.00 (1H, dd)

Example 8

2-(4-Imidazolylmethyl)benzofuro[3,2-d]thiazole

Starting compounds: 2-bromo-3-coumaranone, 4-imidazolyl thioacetamide hydrochloride Melting point: 184°–186° C. (dec.) methanol Elemental analysis data (as $C_{13}H_9N_3OS \cdot 0.1 H_2O$)

|  | C (%) | H (%) | N (%) | S (%) |
|---|---|---|---|---|
| calcd. | 60.73 | 3.61 | 16.34 | 12.47 |
| found | 60.82 | 3.59 | 16.24 | 12.47 |

Mass spectrometry value (m/z): 225 (M$^+$)

Nuclear magnetic resonance spectrum (CDCl$_3$, TMS internal standard) δ: 4.45 (2H, s), 7.02 (1H, s), 7.30–7.37 (2H, m), 7.55 (1H, dd), 7.66 (1H, s), 7.89 (1H, dd)

Example 9

2-(4-Imidazolyl)-8H-indeno[1,2-d]thiazole

Starting compounds: 2-bromo-1-indanone, 4-imidazole carbothioamide

Melting point: 228°–230° C. (dec.) chloroform-diethyl ether

Elemental analysis data (as $C_{13}H_9N_3S \cdot 0.05 H_2O$)

|  | C (%) | H (%) | N (%) | S (%) |
|---|---|---|---|---|
| calcd. | 65.01 | 3.82 | 17.49 | 13.35 |
| found | 65.16 | 3.84 | 17.20 | 13.32 |

Mass spectrometry value (m/z): 239 (M$^+$)

Nuclear magnetic resonance spectrum (DMSO-d$_6$, TMS internal standard ) δ: 3.95 (3H, s), 7.26 (1H, t), 7.38 (1H, t), 7.57 (1H, d), 7.65 (1H, d), 7.79 (1H, s), 7.71 (1H, s)

Example 10

2-(1-Imidazolylmethyl)-8H-indeno[1,2-d]thiazole fumarate

Starting compounds: 2-bromo-1-indanone, 1-imidazolyl thioacetamide hydrochloride Melting point: 155°–159° C. methanol-diethyl ether Elemental analysis data (as $C_{14}H_{11}N_3S \cdot C_4H_4 \cdot 0.1 H_2O$)

|  | C (%) | H (%) | N (%) | S (%) |
|---|---|---|---|---|
| calcd. | 58.24 | 4.13 | 11.32 | 8.64 |
| found | 58.21 | 4.09 | 11.05 | 8.74 |

Mass spectrometry value (m/z): 253 (M$^+$)

Nuclear magnetic resonance spectrum (DMSO-d$_6$, TMS internal standard) δ: 3.93 (2H, s), 5.69 (2H, s), 6.63 (2H, s), 6.98 (1H, s), 7.33 (1H, s), 7.38 (1H, t), 7.28 (1H, t), 7.57 (1H, d), 7.66 (1H, d), 7.89 (1H, s)

Example 11

2-(2-Imidazolylmethyl)-8H-indeno[1,2-d]thiazole fumarate

Starting compounds: 2-bromo-1-indanone, 2-imidazolyl thioacetamide hydrochloride Melting point: 201°–204° C. methanol Elemental analysis data (as $C_{14}H_{11}N_3S \cdot C_4H_4O_4 \cdot 0.3 H_2O$)

|  | C (%) | H (%) | N (%) | S (%) |
|---|---|---|---|---|
| calcd. | 57.60 | 4.20 | 11.21 | 8.56 |
| found | 57.56 | 4.10 | 11.27 | 8.42 |

Mass spectrometry value (m/z): 254 (M$^+$+1)

Nuclear magnetic resonance spectrum (DMSO-d$_6$, TMS internal standard) δ: 3.89 (2H, s), 4.47 (2H, s), 6.63 (2H, s), 7.25 (1H, t), 7.36 (1H, t), 7.56 (1H, d), 7.63 (1H, d)

Example 12

2-[(4-Methyl-5-imidazolyl)methyl]-8H-indeno[1,2-d]thiazole fumarate

Starting compounds: 2-bromo-1-indanone, (5-methyl-4-imidazolyl)thioacetamide hydrochloride Melting point: 169°–172° C. methanol-diethyl ether Elemental analysis data (as $C_{15}H_{13}N_3S \cdot C_4H_4O \cdot 0.45 H_2O$)

|  | C (%) | H (%) | N (%) | S (%) |
|---|---|---|---|---|
| calcd. | 57.80 | 4.58 | 10.42 | 7.95 |
| found | 58.07 | 4.66 | 10.47 | 7.66 |

Mass spectrometry value (m/z): 267 ($M^+$+1)

Nuclear magnetic resonance spectrum (DMSO-$d_6$, TMS internal standard) δ: 2.71 (2H, s), 3.85 (3H, s), 4.26 (2H, s), 6.62 (2H, s), 7.24 (1H, t), 7.34 (1H, t), 7.53 (1H, t), 7.54 (1H, d), 7.62 (1H, d)

Example 13

2-[(2-Methyl-4-imidazolyl)methyl]-8H-indeno[1,2-d]thiazole

Starting compounds: 2-bromo-1-indanone, (2-methyl-4-imidazolyl)thioacetamide hydrochloride Melting point: 187°–190° C. methanol-diethyl ether Elemental analysis data (as $C_{15}H_{13}N_3S \cdot 0.45 H_2O$)

|  | C (%) | H (%) | N (%) | S (%) |
|---|---|---|---|---|
| calcd. | 65.40 | 5.09 | 15.25 | 11.64 |
| found | 65.35 | 4.83 | 15.53 | 11.59 |

Mass spectrometry value (m/z): 267 ($M^+$)

Nuclear magnetic resonance spectrum (DMSO-$d_6$, TMS internal standard) δ: 2.31 (3H, s), 3.87 (2H, s), 4.23 (2H, s), 7.24 (1H, t), 7.36 (1H, t), 7.55 (1H, d), 7.62 (1H, d)

Example 14

2-[(1-Methyl-4-imidazolyl)methyl]-8H-indeno[1,2-d]thiazole

Starting compounds: 2-bromo-1-indanone, (1-methyl-4-imidazolyl)thioacetamide hydrochloride Melting point: 123°–125° C. chloroform-diethyl ether Elemental analysis data (as $C_{15}H_{13}N_3S$)

|  | C (%) | H (%) | N (%) | S (%) |
|---|---|---|---|---|
| calcd. | 67.39 | 4.90 | 15.72 | 11.99 |
| found | 67.17 | 4.94 | 15.49 | 12.09 |

Mass spectrometry value (m/z): 268 ($M^+$+1)

Nuclear magnetic resonance spectrum (CDCl$_3$, TMS internal standard) δ: 3.65 (3H, s), 3.79 (2H, s), 4.40 (2H, s), 6.82 (1H, s), 7.22 (1H, t), 7.36 (1H, t), 7.40 (1H, s), 7.48 (1H, d), 7.70 (1H, d)

Example 15

2-[(1-Methyl-5-imidazolyl)methyl]-8H-indeno[1,2-d]thiazole

Starting compounds: 2-bromo-1-indanone, (1-methyl-5-imidazolyl)thioacetamide hydrochloride Melting point: 148°–151° C. chloroform-diethyl ether Elemental analysis data (as $C_{15}H_{13}N_3S$)

|  | C (%) | H (%) | N (%) | S (%) |
|---|---|---|---|---|
| calcd. | 67.39 | 4.90 | 15.72 | 11.99 |
| found | 67.33 | 4.96 | 15.89 | 11.88 |

Mass spectrometry value (m/z): 268 ($M^+$+1)

Nuclear magnetic resonance spectrum (CDCl$_3$, TMS internal standard) δ: 3.58 (3H, s), 3.80 (2H, s), 4.44 (2H, s), 7.70 (1H, s), 7.26 (1H, t), 7.34 (1H, t), 7.46 (1H, s), 7.50 (1H, d), 7.76 (1H, d)

Example 16

2-[[1-(2-Propyl)-4-imidazolyl]methyl]-8H-indeno[1,2-d]thiazole

Starting compounds: 2-bromo-1-indanone, [1-(2-propyl)-4-imidazolyl]thioacetamide hydrochloride Melting point: 90°–93° C. methanol-diethyl ether Elemental analysis data (as $C_{17}H_{17}N_3S$)

|  | C (%) | H (%) | N (%) | S (%) |
|---|---|---|---|---|
| calcd. | 69.12 | 5.80 | 14.22 | 10.85 |
| found | 69.01 | 5.84 | 14.15 | 10.98 |

Mass spectrometry value (m/z): 295 ($M^+$)

Nuclear magnetic resonance spectrum (CDCl$_3$, TMS internal standard) δ: 1.46 (6H, d), 3.78 (2H, s), 4.29 (1H, m), 4.41 (2H, s), 6.89 (1H, s), 7.22 (1H, t), 7.36 (1H, t), 7.47 (1H, d), 7.77 (1H, d)

Example 17

2-[1-(4-Imidazolyl)ethyl]-8H-indeno[1,2-d]thiazole fumarate

Starting compounds: 2-bromo-1-indanone, 2-(4-imidazolyl)propanethioamide hydrochloride Melting point: 177°–180° C. methanol Elemental analysis data (as $C_{15}H_{13}N_3S \cdot C_4H_4O \cdot 0.1 H_2O$)

|  | C (%) | H (%) | N (%) | S (%) |
|---|---|---|---|---|
| calcd. | 59.24 | 4.50 | 10.91 | 8.32 |
| found | 59.19 | 4.49 | 10.75 | 8.18 |

Mass spectrometry value (m/z): 267 ($M^+$)

Nuclear magnetic resonance spectrum (DMSO-$d_6$, TMS internal standard) δ: 1.71 (3H, d), 3.84 (2H, s), 4.56 (1H, m), 6.63 (2H, s), 7.06 (1H, s), 7.24 (1H, t), 7.36 (1H, t), 7.54 (1H, d), 7.66 (1H, d), 7.69 (1H, s)

Example 18

2-[2-(4-Imidazolyl)ethyl]-8H-indeno[1,2-d]thiazole sesquifumarate

Starting compounds: 2-bromo-1-indanone, 3-(4-imidazolyl)propanethioamide hydrochloride Melting point: 143°–147° C. methanol Mass spectrometry value (m/z): 267 ($M^+$)

Nuclear magnetic resonance spectrum (DMSO-d$_6$, TMS internal standard) δ: 3.03 (2H, t), 3.39 (2H, t), 3.89 (2H, s), 6.62 (3H, s), 6.88 (1H, s), 7.25 (1H, t), 7.36 (1H, t), 7.55 (1H, d), 7.63 (1H, d), 7.70 (1H, s)

Example 19

2-[2-(1-Imidazolyl)ethyl]-8H-indeno[1,2-d]thiazole

Starting compounds: 2-bromo-1-indanone, 3-(1-imidazolyl)propanethioamide hydrochloride Melting point: 118°–121° C. methanol-diethyl ether Elemental analysis data (as C$_{15}$H$_{13}$N$_3$S·0.4 H$_2$O)

|  | C (%) | H (%) | N (%) | S (%) |
| --- | --- | --- | --- | --- |
| calcd. | 65.62 | 5.07 | 15.30 | 11.68 |
| found | 65.74 | 4.90 | 15.13 | 11.60 |

Mass spectrometry value (m/z): 267 (M$^+$)

Nuclear magnetic resonance spectrum (DMSO-d$_6$, TMS internal standard) δ: 3.57 (2H, t), 3.89 (2H, s), 4.49 (2H, t), 7.26 (1H, d), 7.27 (1H, t), 7.37 (1H, t), 7.56 (1H, d), 7.64 (1H, d), 7.71 (1H, s)

Example 20

2-[2-(2-Imidazolyl)ethyl]-8H-indeno[1,2-d]thiazole fumarate

Starting compounds: 2-bromo-1-indanone, 3-(2-imidazolyl)propanethioamide hydrochloride Melting point: 177°–180° C. methanol Mass spectrometry value (m/z): 267 (M$^+$)

Nuclear magnetic resonance spectrum (DMSO-d$_6$, TMS internal standard) δ: 3.15 (2H, t), 3.48 (2H, t), 3.89 (2H, s), 6.62 (2H, s), 6.94 (2H, s), 7.25 (1H, t), 7.36 (1H, t), 7.54 (1H, d), 7.63 (1H, d)

Example 21

2-[3-(1-Imidazolyl)propyl]-8H-indeno[1,2-d]thiazole dihydrochloride

Starting compounds: 2-bromo-1-indanone, 4-(1-imidazolyl)butanethioamide hydrochloride Melting point: 175°–177° C. methanol Elemental analysis data (as C$_{16}$H$_{15}$N$_3$S·2 HCl·0.3 H$_2$O)

|  | C (%) | H (%) | N (%) | S (%) | Cl (%) |
| --- | --- | --- | --- | --- | --- |
| calcd. | 53.43 | 4.93 | 11.68 | 8.91 | 19.71 |
| found | 53.08 | 4.75 | 11.65 | 9.07 | 20.02 |

Mass spectrometry value (m/z): 281 (M$^+$)

Nuclear magnetic resonance spectrum (DMSO-d$_6$, TMS internal standard) δ: 2.3614 2.41 (2H, m), 3.12 (2H, t), 3.92 (2H, s), 4.36 (2H, t), 7.27 (1H, t), 7.37 (1H, t), 7.57 (1H, d), 7.54 (1H, d), 7.71 (1H, s), 7.87 (1H, s), 9.25 (1H, s)

Example 22

2-(4-Imidazolylmethyl)-5-methoxy-8H-indeno[1,2-d]thiazole

Starting compounds: 2-bromo-6-methoxy-1-indanone, 4-imidazolylthioacetamide hydrochloride Melting point: 190°–191° C. ethyl acetate Elemental analysis data (as C$_{15}$H$_{13}$N$_3$OS·0.1 H$_2$O)

|  | C (%) | H (%) | N (%) | S (%) |
| --- | --- | --- | --- | --- |
| calcd. | 63.18 | 4.67 | 14.74 | 11.25 |
| found | 63.06 | 4.64 | 14.64 | 11.29 |

Mass spectrometry value (m/z): 270 (M$^+$+1)

Nuclear magnetic resonance spectrum (DMSO-d$_6$, TMS internal standard) δ: 3.78 (2H, s), 3.81 (3H, s), 4.31 (2H, s), 6.80 (1H, dd), 7.04 (1H, s), 7.18 (1H, d), 7.42 (1H, d), 7.64 (1H, s), 12.10 (1H, br)

Example 23

2-(4-Imidazolylmethyl)-8-nitro-4,5-dihydronaphtho[1,2-d]thiazole

Starting compounds: 2-bromo-7-nitro-1-tetralone, 4-imidazolylthioacetamide hydrochloride Melting point: 230°–233° C. (dec.) ethyl acetate Elemental analysis data (as C$_{15}$H$_{12}$N$_4$O$_2$S·0.2 H$_2$O)

|  | C (%) | H (%) | N (%) | S (%) |
| --- | --- | --- | --- | --- |
| calcd. | 57.02 | 3.96 | 17.73 | 10.15 |
| found | 57.15 | 3.90 | 17.45 | 10.06 |

Mass spectrometry value (m/z): 313 (M$^+$+1)

Nuclear magnetic resonance spectrum (DMSO-d$_6$, TMS internal standard) δ: 3.04 (2H, t), 3.14 (2H, t), 4.27 (2H, s), 7.06 (1H, s), 7.56 (1H, d), 7.63 (1H, s), 8.07 (1H, dd), 8.46 (1H, d), 12.03 (1H, br)

Example 24

2-(4-Imidazolylmethyl)-6-methoxy-4,5-dihydronaphtho[1,2-d]thiazole

Starting compounds: 2-bromo-5-methoxy-1-tetralone, 4-imidazolylthioacetamide hydrochloride Melting point: 187°–190° C. (dec.) ethyl acetate Mass spectrometry value (m/z): 298 (M$^+$+1)

Nuclear magnetic resonance spectrum (DMSO-d$_6$, TMS internal standard) δ: 2.92 (4H, s), 3.81 (3H, s), 4.22 (2H, s), 6.92 (1H, d), 7.03 (1H, s), 7.25 (1H, t), 7.42 (1H, d), 7.61 (1H, s), 12.00 (1H, br)

Example 25

2-(4-Imidazolylmethyl)-10,11-dihydrophenanthro[1,2-d]thiazole

Starting compounds: 2-bromo-1,2,3,4-tetrahydrophenanthren-1-one, 4-imidazolylthioacetamide hydrochloride Melting point: 225°–230° C. (dec.) methanol Elemental analysis data (as C$_{19}$H$_{15}$N$_3$S·0.4 H$_2$O)

|  | C (%) | H (%) | N (%) | S (%) |
| --- | --- | --- | --- | --- |
| calcd. | 70.30 | 4.91 | 12.94 | 9.88 |
| found | 70.30 | 4.97 | 12.78 | 9.67 |

Mass spectrometry value (m/z ): 317 (M$^+$)

Nuclear magnetic resonance spectrum (DMSO-$d_6$, TMS internal standard) δ: 3.11 (2H, t), 3.43 (2H, t), 4.26 (2H, s), 7.05 (1H, s), 7.48 (1H, t), 7.56 (1H, dt), 7.62 (1H, s), 7.86 (1H, d), 7.91 (1H, d), 8.05 (1H, d), 8.15 (1H, d), 12.01 (1H, br)

Example 26

5-Fluoro-2-(4-imidazolylmethyl)-8H-indeno[1,2-d]thiazole

Starting compounds: 2-bromo-6-fluoro-1-indanone, 4-imidazolylthioacetamide hydrochloride Melting point: 175°–178° C. ethyl acetate Mass spectrometry value (m/z): 271 (M$^+$)

Nuclear magnetic resonance spectrum (DMSO-$d_6$, TMS internal standard) δ: 3.86 (2H, s), 4.32 (2H, s), 7.05 (1H, dd), 7.06 (2H, s), 7.40 (1H, dd), 7.55 (1H, dd), 7.65 (1H, s)

Example 27a

7-Benzoyloxy-2-(4-imidazolylmethyl)-8H-indeno[1,2-d]thiazole 0.8 hydrochloride-1.2 hydrobromide Starting compounds: 4-benzoyloxy-2-bromo-1-indanone, 4-imidazolylthioacetamide hydrochloride Melting point: 220°–225° C, (dec.) 2-propanol Elemental analysis data (as $C_{21}H_{15}N_3O_2S \cdot 0.8$ HCl$\cdot 1.2$ HBr)

|  | C (%) | H (%) | N (%) | S (%) | Cl (%) | Br (%) |
|---|---|---|---|---|---|---|
| calcd. | 50.48 | 3.43 | 8.41 | 6.42 | 5.68 | 19.19 |
| found | 50.12 | 3.43 | 8.31 | 6.55 | 5.24 | 18.95 |

Mass spectrometry value (m/z): 374 (M$^+$+1)

Nuclear magnetic resonance spectrum (DMSO-$d_6$, TMS internal standard) δ: 3.91 (2H, s), 4.62 (2H, s), 7.25 (1H, d), 7.51 (1H, t), 7.61–7.67 (4H, m), 7.80 (1H, t), 8.21 (1H, d), 9.11 (1H, s)

Example 27b 1 ml of a 5N aqueous sodium hydroxide solution was added to a solution of 0.358 g of 7-benzoyloxy-2-(4-imidazolylmethyl)- 8H-indeno[1,2-d]thiazole hydrochloride-hydrobromide obtained in Example 27a in methanol (10 ml), and the mixture was stirred at room temperature for 30 minutes. After evaporation of the solvent, the residue was acidified with 1N hydrochloric acid, neutralized with sodium bicarbonate and then extracted with chloroform-methanol. The organic layer was dried over anhydrous magnesium sulfate, the solvent was evaporated, and the resultant crude crystals (0.20 g) were recrystallized from ethanol to obtain 77 mg of 7-hydroxy-2-(4-imidazolylmethyl)-8H-indeno[1,2-d]thiazole.

Melting point: 250°–255° C. (dec.) ethanol

Elemental analysis data (as $C_{14}H_{11}N_3OS$)

|  | C (%) | H (%) | N (%) | S (%) |
|---|---|---|---|---|
| calcd. | 62.43 | 4.12 | 15.60 | 11.91 |
| found | 62.33 | 4.10 | 15.47 | 11.94 |

Mass spectrometry value (m/z): 270 (M$^+$+1)

Nuclear magnetic resonance spectrum (DMSO-$d_6$, TMS internal standard) δ: 3.71 (2H, s), 4.30 (2H, s), 6.72 (1H, d), 7.03 (1H, s), 7.12 (1H, d), 7.19 (1H, t), 7.61 (1H, s), 9.62 (1H, s), 11.99 (1H, br)

Example 28

0.1 ml of bromine was added dropwise to a solution of 0.47 g of 7-benzoyloxy-1-indanone in tetrahydrofuran (10 ml) at room temperature, and the mixture was stirred for 30 minutes. To 7-benzoyloxy-2-bromo-1-indanone obtained by evaporation of the solvent was added 15 ml of 2-propanol and 0.33 g of 4-imidazolylthioacetamide hydrochloride, followed by 2.5 hours of heating under reflux. After cooling and evaporation of the solvent, the residue was mixed with ethyl acetate, and extracted with 1N hydrochloric acid. The aqueous layer was neutralized with sodium bicarbonate and then extracted with chloroform. The organic layer was dried over anhydrous magnesium sulfate and the solvent was evaporated. The residual 4-benzoyloxy-2-(4-imidazolylmethyl)-8H-indeno[1,2-d]thiazole was dissolved in 10 ml of methanol, to the solution was added 1 ml of 5N aqueous sodium hydroxide solution and then stirred at room temperature for 15 minutes. After acidifying with 1N hydrochloric acid, the reaction solution was neutralized with sodium bicarbonate, and extracted with chloroform-methanol, and then the extract was dried over anhydrous magnesium sulfate. After evaporation of the solvent, the resultant crude crystals were recrystallized from ethanol to obtain 55 mg of 4-hydroxy-2-(4-imidazolylmethyl)-8H-indeno[1,2-d]thiazole.

Melting point: 267°–269° C. (dec.) ethanol

Elemental analysis data (as $C_{14}H_{11}N_3OS \cdot 0.3$ $H_2O$)

|  | C (%) | H (%) | N (%) | S (%) |
|---|---|---|---|---|
| calcd. | 61.21 | 4.26 | 15.30 | 11.67 |
| found | 61.23 | 4.15 | 15.01 | 11.96 |

Mass spectrometry value (m/z): 269 (M$^+$)

Nuclear magnetic resonance spectrum (DMSO-$d_6$, TMS internal standard) δ: 3.80 (2H, s), 4.30 (2H, s), 6.81 (1H, d), 6.98–7.06 (3H, m), 7.60 (1H, s), 9.51 (1H, s), 11.98 (1H, br)

Example 29

5.0 g of Raney nickel (wet) was added to a solution of 0.52 g of.2-(4-imidazolylmethyl)-8-nitro-4,5-dihydronaphtho[1,2-d]thiazole obtained in Example 23 in 1,4-dioxane (40 ml)-methanol (20 ml), and the mixture was stirred for 2 hours in an atmosphere of hydrogen (1 atm). After filtration of insoluble matter, the solvent was evaporated from the filtrate, and the residue was mixed with ethyl acetate to effect crystallization. The resultant crude crystals were washed with hot ethyl acetate to afford 0.27 g (57%) of 8-amino-2-(4-imidazolylmethyl)-4,5-dihydronaphtho[1,2-d]thiazole.

Melting point: 180°–182° C. ethyl acetate

Elemental analysis data (as $C_{15}H_{14}N_4S \cdot 0.4$ $H_2O$)

|  | C (%) | H (%) | N (%) | S (%) |
|---|---|---|---|---|
| calcd. | 62.22 | 5.15 | 19.35 | 11.07 |
| found | 62.17 | 4.90 | 19.15 | 11.03 |

Mass spectrometry value (m/z): 282 (M$^+$)

Nuclear magnetic resonance spectrum (DMSO-d$_6$, TMS internal standard) δ: 2.78 (2H, t), 2.85 (2H, t), 4.18 (2H, s), 4.98 (2H, s), 6.40 (1H, dd), 6.88 (1H, d), 7.04 (1H, brs), 7.09 (1H, d), 7.60 (1H, s), 11.96 (1H, br)

Reference Example 15

To 3.98 g of 2-methylnaphtho[1,2-d]thiazole dissolved in carbon tetrachloride (40 ml) was added 3.56 g of N-bromosuccinimide and 0.20 g of benzoyl peroxide, followed by 6 hours of heating under reflux. After cooling the reaction solution, insoluble matter was removed by filtration, and the solvent was evaporated. The residue was subjected to silica gel column chromatography eluted with hexane-chloroform (5:1) to obtain 3.50 g (63%) of 2-bromomethylnaphtho[1,2-d]thiazole.

Mass spectrometry value (m/z): 277, 279 (M$^+$)

Nuclear magnetic resonance spectrum (CDCl$_3$, TMS internal standard) δ: 4.94 (2H, s), 7.5–7.7 (2H, m), 7.8–8.0 (3H, m), 8.77 (1H, dd)

Example 30

0.06 g of sodium hydride (60%) was added to a solution of 0.10 g of imidazole in tetrahydrofuran (30 ml). After 30 minutes of stirring at room temperature, a solution of 2-bromomethylnaphtho[1,2-d]thiazole in tetrahydrofuran (10 ml) was added to the solution. After stirring at room temperature for 1 hour and evaporation of the solvent, the residue was partitioned between 1N hydrochloric acid and ethyl acetate. The organic layer was extracted with 1N hydrochloric acid. The combined aqueous layer was neutralized with sodium bicarbonate and then extracted with chloroform. After drying over anhydrous magnesium sulfate, the solvent was evaporated to obtain 0.27 g (100%) of 2-(1-imidazolylmethyl)naphtho[1,2-d]thiazole. This free base was dissolved in methanol and mixed with 0.10 g of fumaric acid to effect crystallization to give 0.32 g of fumarate.

Melting point: 163°–165° C. methanol

Elemental analysis data (as C$_{15}$H$_{11}$N$_3$S·C$_4$H$_4$O$_4$)

|  | C (%) | H (%) | N (%) | S (%) |
|---|---|---|---|---|
| calcd. | 59.83 | 3.96 | 11.02 | 8.41 |
| found | 59.83 | 3.91 | 10.93 | 8.38 |

Mass spectrometry value (m/z): 265 (M$^+$)

Nuclear magnetic resonance spectrum (DMSO-d$_6$, TMS internal standard) δ: 5.88 (2H, s), 6.64 (2H, s), 7.04 (1H, s), 7.43 (1H, s), 7.65 (1H, t), 7.73 (1H, t), 7.95 (1H, d), 7.97 (1H, s), 8.09 (1H, d), 8.13 (1H, d), 8.65 (1H, d)

The following compound was obtained in the same manner as described in Example 1.

Example 31

8-Cyano-2-(4-imidazolylmethyl)-4,5-dihydronaphtho[1,2-d]thiazole

Starting compounds: 2-bromo-7-cyano-1-tetralone, 4-imidazolylthioacetamide hydrochloride Melting point: 201°–205° C. methanol-ethyl acetate Elemental analysis data (as C$_{16}$H$_{12}$N$_4$S·0.2 H$_2$O)

|  | C (%) | H (%) | N (%) | S (%) |
|---|---|---|---|---|
| calcd. | 64.93 | 4.22 | 18.93 | 10.83 |
| found | 65.00 | 4.26 | 18.64 | 10.81 |

Mass spectrometry value (m/z): 292 (M$^+$)

Infrared absorption spectrum (KBr) cm$^{-1}$: 2228 (C≡N)

Nuclear magnetic resonance spectrum (DMSO-d$_6$, TMS internal standard) δ: 3.00 (2H, t), 3.08 (2H, t), 4.23 (2H, s), 7.07 (1H, s), 7.49 (1H, d), 7.61 (1H, s), 7.66 (1H, dd), 8.01 (1H, s), 11.96 (1H, br)

Structures of the compounds of Examples are shown in the following table.

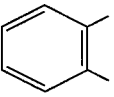

| Ex. No. | R | Ring A | L$_1$ | L$_2$ | L | Im | Salt, etc. |
|---|---|---|---|---|---|---|---|
| 1 | H | 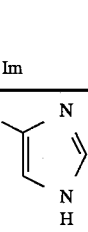 | — | —CH$_2$— | —CH$_2$— | (imidazole) | Fumarate |
| 2 | " | " | —CH$_2$— | — | " | " | 1/2 Fumarate |
| 3 | " | " | — | —(CH$_2$)$_2$— | " | " | Fumarate |
| 4 | " | " | " | —(CH$_2$)$_3$— | " | " | " |
| 5 | " | " | " | —CH—CH$_2$—<br>\|<br>CH$_3$ | " | " | free |
| 6 | " | " | " | —O—CH$_2$— | " | " | Fumarate |
| 7 | " | " | " | —S—CH$_2$— | " | " | free |

-continued

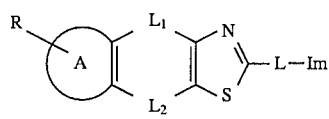

| Ex. No. | R | Ring A | $L_1$ | $L_2$ | L | Im | Salt, etc. |
|---|---|---|---|---|---|---|---|
| 8 | " | " | " | —O— | " | " | " |
| 9 | " | " | " | —CH$_2$— | — | " | " |
| 10 | " | " | " | " | —CH$_2$— | imidazol-1-yl | Fumarate |
| 11 | H | benzene | — | —CH$_2$— | —CH$_2$— | 2-(1H-imidazolyl) | Fumarate |
| 12 | " | " | " | " | " | 4,5-dimethyl-1H-imidazolyl | " |
| 13 | " | " | " | " | " | 2-methyl-1H-imidazolyl | free |
| 14 | " | " | " | " | " | 1-methylimidazolyl | " |
| 15 | " | " | " | " | " | 1-methylimidazolyl (other isomer) | " |
| 16 | " | " | " | " | " | 1-isopropylimidazolyl | " |
| 17 | " | " | " | " | —CH(CH$_3$)— | 1H-imidazolyl | Fumarate |
| 18 | " | " | " | " | —(CH$_2$)$_2$— | 1H-imidazolyl | 3/2 Fumarate |
| 19 | " | " | " | " | " | imidazol-1-yl | free |

-continued

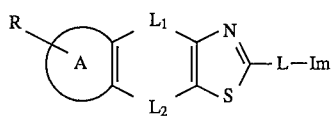

| Ex. No. | R | Ring A | $L_1$ | $L_2$ | L | Im | Salt, etc. |
|---|---|---|---|---|---|---|---|
| 20 | " | " | " | " | " | ![imidazole] | Fumarate |
| 21 | H | ![benzene] | — | $-CH_2-$ | $-(CH_2)_3-$ | ![imidazole] | 2HCl |
| 22 | $5-CH_3O-$ | " | " | " | $-CH_2-$ | ![imidazole] | free |
| 23 | $8-NO_2-$ | " | " | $-(CH_2)_2-$ | " | " | " |
| 24 | $6-CH_3O-$ | " | " | " | " | " | " |
| 25 | H | ![naphthalene] | " | " | " | " | " |
| 26 | 5-F | ![benzene] | " | $-CH_2-$ | " | " | " |
| 27a | 7-PhCOO— | " | " | " | " | " | 0.8 HCl 1.2 HBr |
| 27b | 7-HO— | " | " | " | " | " | free |
| 28a | 4-PhCOO— | " | " | " | " | " | " |
| 28b | 4-HO— | " | " | " | " | " | " |
| 29 | $8-NH_2-$ | " | " | $-(CH_2)_2-$ | " | " | " |
| 30 | H | " | " | $-CH=CH-$ | " | ![imidazole] | Fumarate |
| 31 | 8-CN | " | " | $-(CH_2)_2-$ | " | ![imidazole] | free |

In addition to the compounds illustrated above, other compounds of the present invention are shown in the following table. These compounds do not require special experiments, because they can be synthesized in accordance with the synthetic pathways and methods described in the above-mentioned production schemes and Examples, as well as their modifications known to one ordinary skilled in the art.

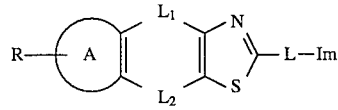

| Ex. No. | R | Ring A | L₁ | L₂ | L | Im |
|---|---|---|---|---|---|---|
| B-1 | H | (benzene) | — | $-CH_2-$ | $-(CH_2)_4-$ | (imidazole) |
| 2 | " | " | " | " | $-(CH_2)_5-$ | " |
| 3 | 4-OMe | " | " | " | $-CH_2-$ | (NH-imidazole) |
| 4 | H | " | " | " | " | (N-Et imidazole) |
| 5 | " | (naphthalene) | " | " | " | (NH-imidazole) |
| 6 | " | (benzene) | " | $-CH(CH_3)-$ | " | " |
| 7 | " | " | " | $-C(CH_3)_2-$ | " | " |
| 8 | " | " | " | $-CH=CH-$ | " | " |
| 9 | 7-CN | " | " | $-CH_2-$ | " | " |
| 10 | 6-CN | " | " | " | " | " |
| B-11 | 5-CN | (benzene) | — | $-CH_2-$ | $-CH_2-$ | (NH-imidazole) |
| 12 | 6-CO₂Me | " | " | " | " | " |
| 13 | 7-COOH | " | " | " | " | " |
| 14 | 4-COOH | " | " | " | " | " |

We claim:
1. A condensed thiazole derivative represented by the following general formula (I) or a pharmaceutically acceptable salt thereof:

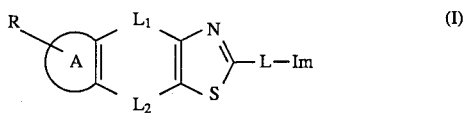

wherein each symbol in the formula has the following meaning;

R is a hydrogen atom, a halogen atom, a hydroxyl group, a lower alkoxy group, a carboxy group, a lower alkoxycarbonyl group, a nitro group, an amino group, a cyano group or a protected hydroxyl group, Ⓐ is a phenyl ring or a naphthalene ring, $L_1$ and $L_2$ are defined so that one is a direct bond and the other is
  a) a straight- or branched-lower alkylene group which may contain an interrupting oxygen or sulfur atom therein,
  b) an oxygen atom or a sulfur atom, or c) a lower alkenylene group, L is a direct bond or a straight- or branched-lower alkylene group, Im is a group represented by a formula:

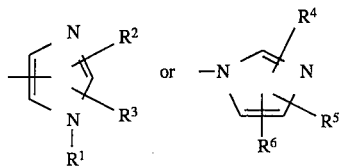

$R^1$, $R^2$ and $R^3$ are the same or different from one another, each representing a hydrogen atom or a lower alkyl group, and $R^4$, $R^5$ and $R^6$ are the same or different from one another, each representing a hydrogen atom or a lower alkyl group.

2. The compound according to claim 1 wherein Ⓐ is a phenyl ring, $L_1$ is a direct bond and $L_2$ is a straight- or branched-lower alkylene group or a lower alkenylene group.

3. 2-(4-Imidazolylmethyl)-8H-indeno[1,2-d]thiazole or a pharmaceutically acceptable salt thereof.

4. 2-(4-Imidazolylmethyl)-4,5-dihydronaphtho[1,2-d] thiazole or a pharmaceutically acceptable salt thereof.

5. A pharmaceutical composition which comprises an effective amount of the condensed thiazole derivative (I) or a pharmaceutically acceptable salt thereof according to claim 1 and a pharmaceutically acceptable carrier.

6. The pharmaceutical composition according to claim 5, which is a 5-HT$_3$ receptor agonist.

7. A process for producing the condensed thiazole derivative (I) or a pharmaceutically acceptable salt thereof according to claim 1, which comprises, reacting an α-halogenoketone represented by a general formula (IIa):

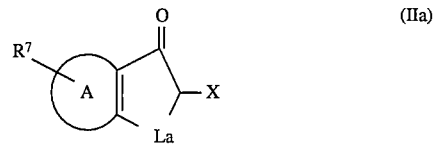

wherein $R^7$ is as defined for R and may be protected, by a protecting group La is a) a straight- or branched-lower alkylene group which may contain an interrupting oxygen or sulfur atom therein, b) an oxygen atom or a sulfur atom or c) a lower alkenylene group, and X is a halogen atom, or by a general formula (IIb):

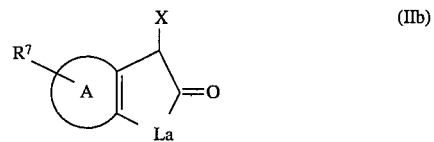

wherein $R^7$, La and X are as defined above with a thioamide derivative represented by a general formula (III):

or a salt thereof, and then eliminating the protecting group when required.

* * * * *